United States Patent [19]
Gero

[11] Patent Number: 5,741,217
[45] Date of Patent: Apr. 21, 1998

[54] BIOFEEDBACK APPARATUS

[76] Inventor: Jeffrey Gero, 5907 Carell Ave., Agoura Hills, Calif. 91301

[21] Appl. No.: 688,512

[22] Filed: Jul. 30, 1996

[51] Int. Cl.$^6$ .................................................. A61B 5/05
[52] U.S. Cl. ............................................ 600/547; 600/587
[58] Field of Search ..................................... 128/774, 782, 128/734

[56] References Cited

U.S. PATENT DOCUMENTS

| | | |
|---|---|---|
| 3,648,686 | 3/1972 | Payne . |
| 3,737,670 | 6/1973 | Larson . |
| 3,855,998 | 12/1974 | Hidalgo-Briceno . |
| 3,870,034 | 3/1975 | James . |
| 3,942,516 | 3/1976 | Glynn et al. . |
| 4,088,125 | 5/1978 | Forgione et al. . |
| 4,461,301 | 7/1984 | Ochs . |
| 4,509,531 | 4/1985 | Ward . |
| 4,632,126 | 12/1986 | Aguilar . |
| 4,690,142 | 9/1987 | Ross et al. . |
| 4,800,893 | 1/1989 | Ross et al. . |
| 4,812,126 | 3/1989 | Gilliksen . |
| 5,253,168 | 10/1993 | Berg . |
| 5,343,871 | 9/1994 | Bittman et al. . |
| 5,426,411 | 6/1995 | Rackman et al. . |
| 5,465,729 | 11/1995 | Bittman et al. . |

OTHER PUBLICATIONS

"Marin Investor Bets on an Impulse", *San Francisco Examiner and Chronicle*, Jul. 2, 1995, p. B1.

*Primary Examiner*—Max Hindenberg
*Assistant Examiner*—Pamela L. Wingood
*Attorney, Agent, or Firm*—Blakely, Sokoloff, Taylor & Zafman

[57] ABSTRACT

Biofeedback monitoring and training of a subject using a computer and a computer mouse in the workplace is achieved by monitoring the galvanic skin response (GSR) of the subject every time he or she uses the mouse and by implementing a predetermined course of action on the computer monitor when measured GSR levels are outside of predetermined upper and lower limits. Biofeedback apparatus for implementing this technique includes a computer mouse with electrodes on the exterior surface of the mouse. When the user makes physical contact with two or more electrodes on the mouse, a very small electrical current is conducted by the subject's skin and is measured. The measured value is transmitted to the computer over a serial communication cable. The mouse otherwise functions as a conventional computer mouse. Software in the computer uses the GSR measurement and implements a predetermined course of action, such as a relaxing message with visual images and soft music. This process can help the subject monitor his or her physiological state in order to increase relaxation.

13 Claims, 4 Drawing Sheets

BIOFEEDBACK APPARATUS

BACKGROUND OF THE INVENTION

1. Field of the Invention

This invention relates generally to biofeedback techniques and apparatus; and more particularly is directed towards a new and convenient method for monitoring the galvanic skin resistance (GSR) of a subject while the subject is using a computer and computer mouse in the workplace or at home.

2. Description of the Prior Art

It has been determined that human beings can learn to control their physiology by using biofeedback instruments. Conventional biofeedback techniques are employed to monitor the degree of autonomic arousal by measuring changes in skin resistance in the subject. A subject who has been exposed to a stressful situation will display a sudden drop in resistance between two areas of the skin. The utilization of a biofeedback instrument has been proven to be useful in teaching individuals to reduce the activation of the body's autonomic stress response and increase the relaxation response.

Various biofeedback devices and methods are disclosed in the prior art. U.S. Pat. No. 3,855,998 issued to Hidalgo-Briceno discloses an entertainment device that monitors electro-physiological parameters of a human subject and presents audio visual stimulation comprising passages of music, flashing lights or projected images intended to place the subject in a desired physiological state. U.S. Pat. No. 3,942,516 issued to Glynn, et al. discloses a system in which a plurality of electro-physiological parameters are simultaneously monitored to produce an audio visual output for feedback. U.S. Pat. No. 5,253,168 issued to Berg discloses a system with which a subject can utilize biofeedback to generate creative audio visual expressions. U.S. Pat. Nos. 5,343,871 and 5,465,729 issued to Bittman, et al. disclose a biofeedback method and apparatus in which measurements of electro-physiological quantities are used to control the presentation to the subject of a series of prestored audio visual sequences.

A mouse is a pointing device commonly used to navigate through computer software. It is typically gripped by one of the user's hands. As the user moves his hand, the physical motion manipulates an icon on the computer screen. The basic features of a mouse consists of a casing with a flat bottom, designed to be gripped by one hand. On the top of the mouse there are one or more push buttons which when depressed select a program, a menu option, find placement on the screen or perform other related functions. This action is typically referred to as a "mouse click." On the bottom of the casing, a small track ball is mounted which rolls as the user slides the mouse across the flat surface. The track ball thus measures the physical motion and transmits this information to the computer through a cable that connects the mouse to the computer.

It is a principal object of this invention to combine the functionality of a computer mouse with a GSR monitoring and feedback system to provide a unique and useful way to monitor and help relieve stress and tension while the subject works on his or her computer.

SUMMARY OF THE INVENTION

This invention relates to a method and associated apparatus for monitoring GSR readings while also providing the functionality of a computer mouse pointing device or other manually operated input device. The GSR measurements are acquired by applying a small electrical voltage across two electrodes located on the surface of the mouse. Upon physical contact of the user's hand with the electrodes, the resulting current through the subject's skin is measured and amplified by an electronic circuit located in the mouse. This signal is eventually converted from its analog form to a digital format which is transmitted upon request to the host computer. Software in the computer then executes predetermined functions based upon the levels of measurement.

DETAILED DESCRIPTION OF THE INVENTION

Figure 1:
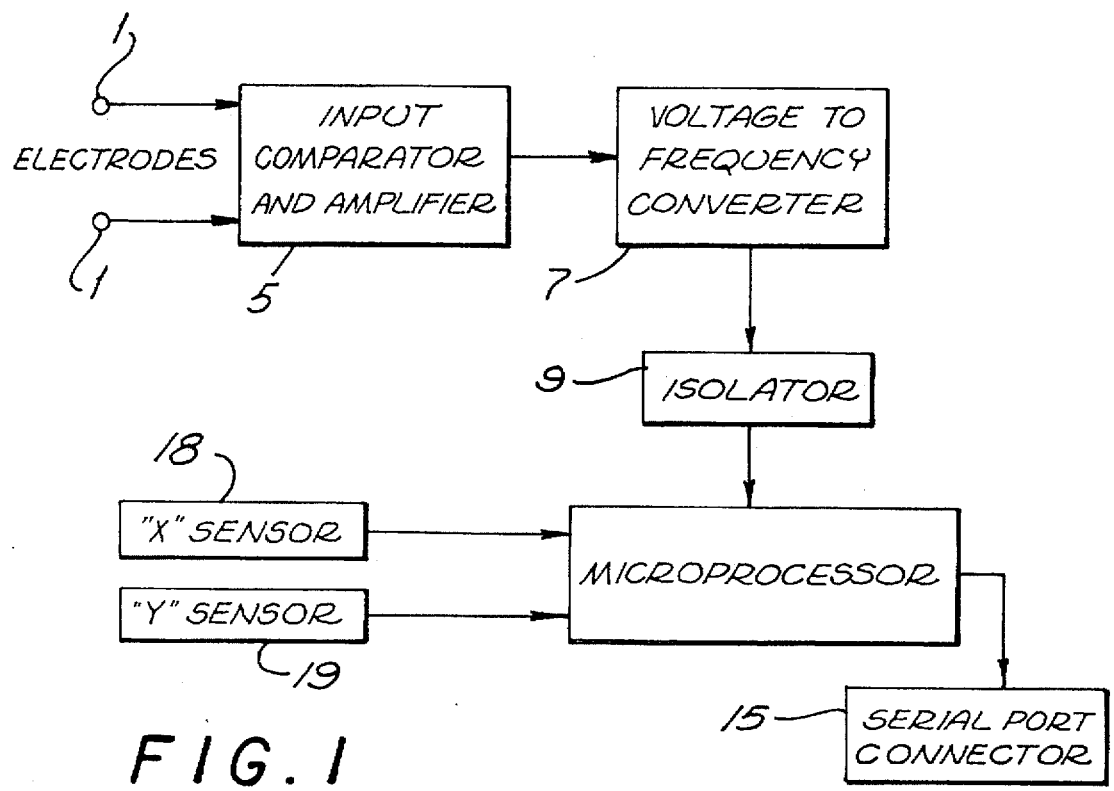
FIG. 1 is a block diagram of a GSR-sensing mouse system in accordance with the invention.

Referring now to the drawings and to FIG. 1 in particular, one embodiment of the present invention comprises a computer mouse. Electrodes 1 are disposed on the surface of the mouse so as to be in contact with the user's skin. Contact with electrodes 1 completes an electrical circuit by which the galvanic skin resistance (GSR) of the user is sensed by input comparator and amplifier 5 which provides a voltage proportional to the GSR of the user. Voltage to frequency converter 7 produces an output waveform in the range of approximately 25 Hz to 476 Hz, the specific frequency being a function of the sensed GSR. This signal is applied to isolator 9, the output of which is received by microprocessor 12. The X and Y position sensors of the mouse also provide inputs to microprocessor 12. The X and Y position signals and the GSR value are output serially to serial port connector 15 which is coupled to the serial input port of the computer (not shown).

Figure 2:
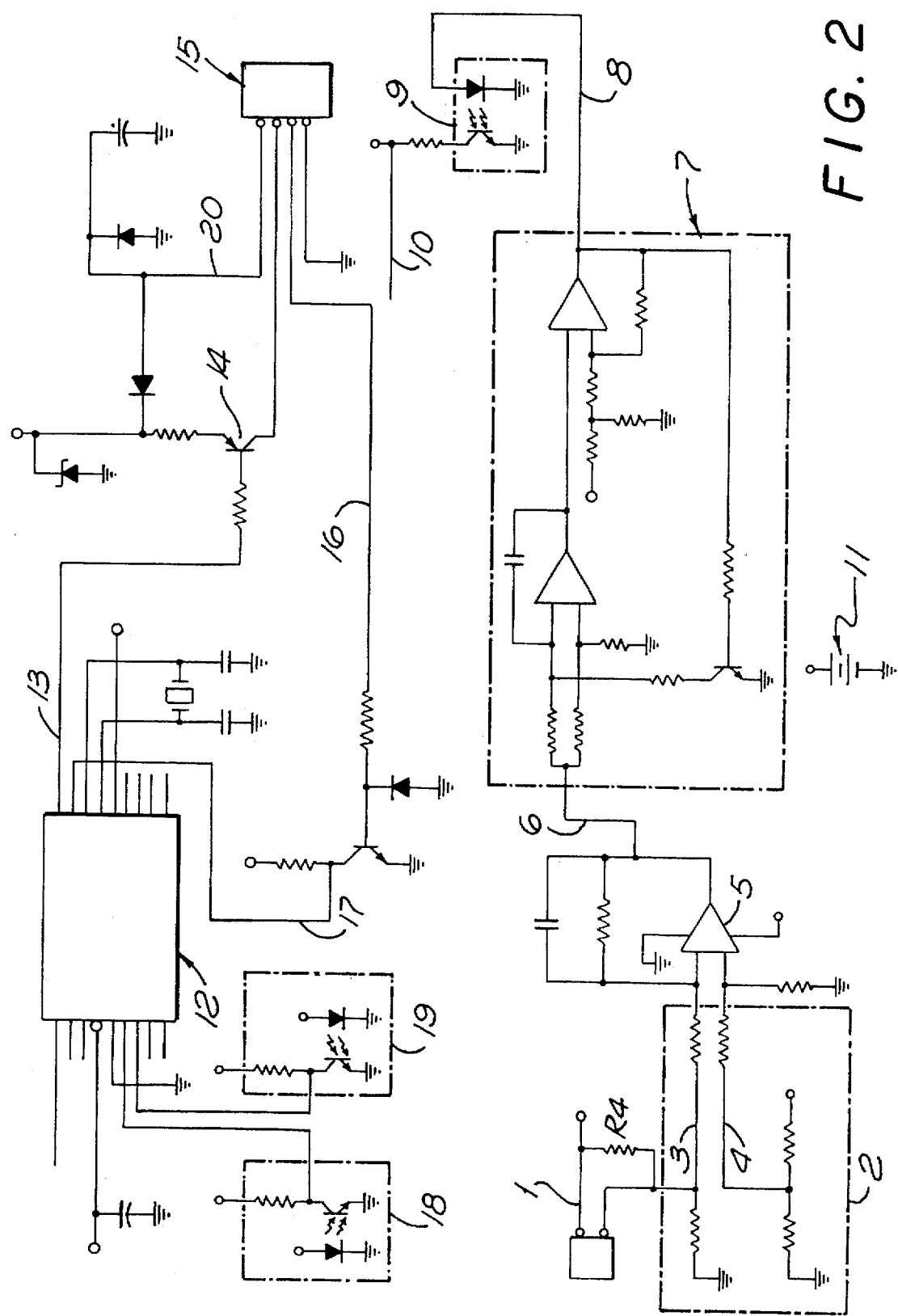
FIG. 2 is a circuit diagram of the GSR-sensing mouse system.

Referring now to FIG. 2, the circuitry for implementing the above-described functions is shown in greater detail. The skin potential of the subject is measured at the electrodes 1, which are physically mounted on the exterior surface of the mouse. The subject's skin resistance appears in parallel to resistance R4 so that the voltage at node 3 is a direct function of the subject's GSR. Node 3 is connected to an H-bridge circuit 2 which provides very high sensitivity to small changes in voltage potential. The voltage at node 3 is compared to a fixed reference voltage 4 by introducing these two signals into a comparator 5. The comparator amplifies the difference between the voltage at node 3 and the reference voltage potential 4 and produces a direct current (DC) voltage 6 in the range of 0 to 5 volts which is linearly and directly proportional to the subject's GSR signal. This DC voltage 6 is fed into a voltage controlled oscillator (VCO) circuit 7, whose output 8 is a square wave. As the DC voltage changes in magnitude, the VCO's output signal 8 will change proportionally in pulse width or frequency. The VCO's output signal 8 is connected to an optical isolation circuit 9 which consists of an LED and phototransistor. All of the circuitry described so far is powered by a 5 volt battery 11.

The output of the optical isolation circuit 10 is fed into a digital input of the microprocessor 12. This microprocessor contains internal memory and is internally programmed to measure the frequency of the VCO's output signal 8 through the optical isolation circuit 9. Within the internal programming of the microprocessor, a 16-bit number is created which is a digital representation of the subject's skin voltage potential. One of the output pins 13 of the microprocessor is used by the internal program to transmit the 16-bit number in a serial fashion compatible with the RS-232 serial communications protocol. This serial signal 13 is buffered through a transistor 14 and is connected to the serial port connector 15. This serial port is connected through a cable to the host computer's serial port. The serial port connector 15 also provides an input signal 16 which is transistor buffered and connected to an input pin 17 of the microprocessor. The internal programming of the microprocessor monitors the RS-232 serial communication protocol compliant signal and responds to pre-defined command characters.

To provide the conventional functionality of a mouse, two optical sensors 18 and 19 are connected to two input pins of the microprocessor 12. The internal programming of the microprocessor measures the data from these two sensors and transmits mouse movement information serially on output pin 13.

The previously described circuit is powered by −12 volts from another pin on the serial port connector 15, and is converted to +5 volts. This voltage source is used to power the microprocessor.

Figure 3:
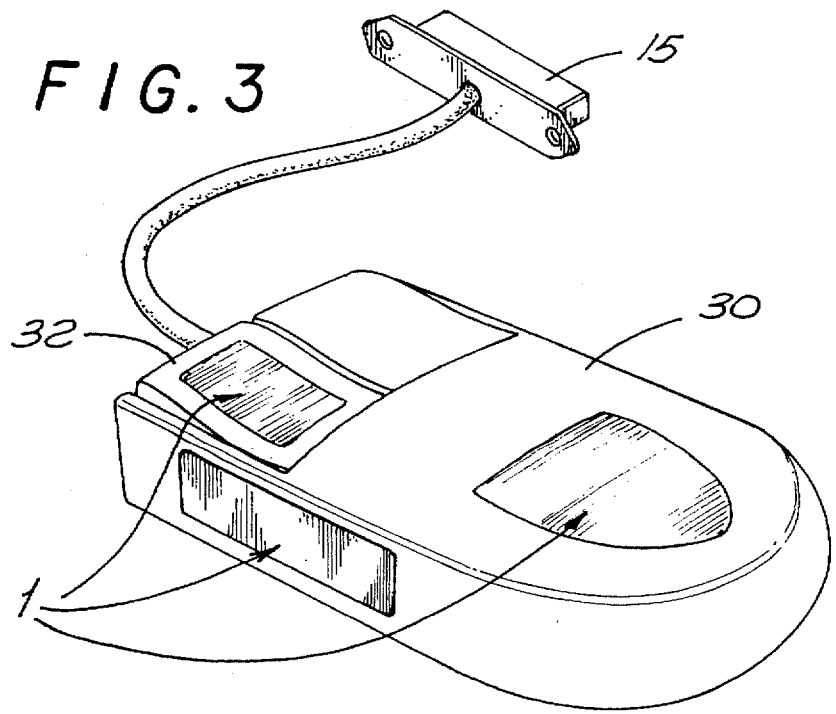
FIG. 3 is a perspective view of a GSR-sensing mouse apparatus in accordance with the invention.

FIG. 3 illustrates the possible placement of electrodes 1 on the outer surface of a computer mouse 30. The electrodes are preferably placed where they will be in intimate contact with the subject's skin during normal usage of mouse 30. It should be noted that continuous contact with the subject's skin is not required. Thus, an electrode may be placed, for example, on button 32 where contact with the subject's skin may only be intermittent.

Figure 4:
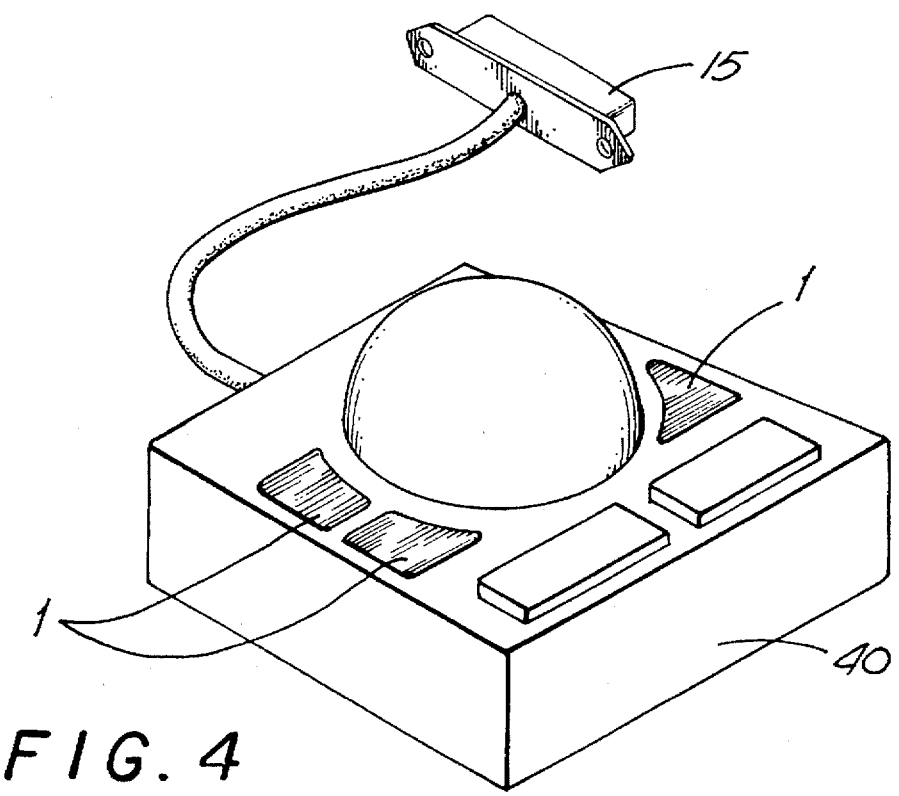
FIG. 4 illustrates a GSR-sensing track ball in accordance with the invention.
Figure 5:
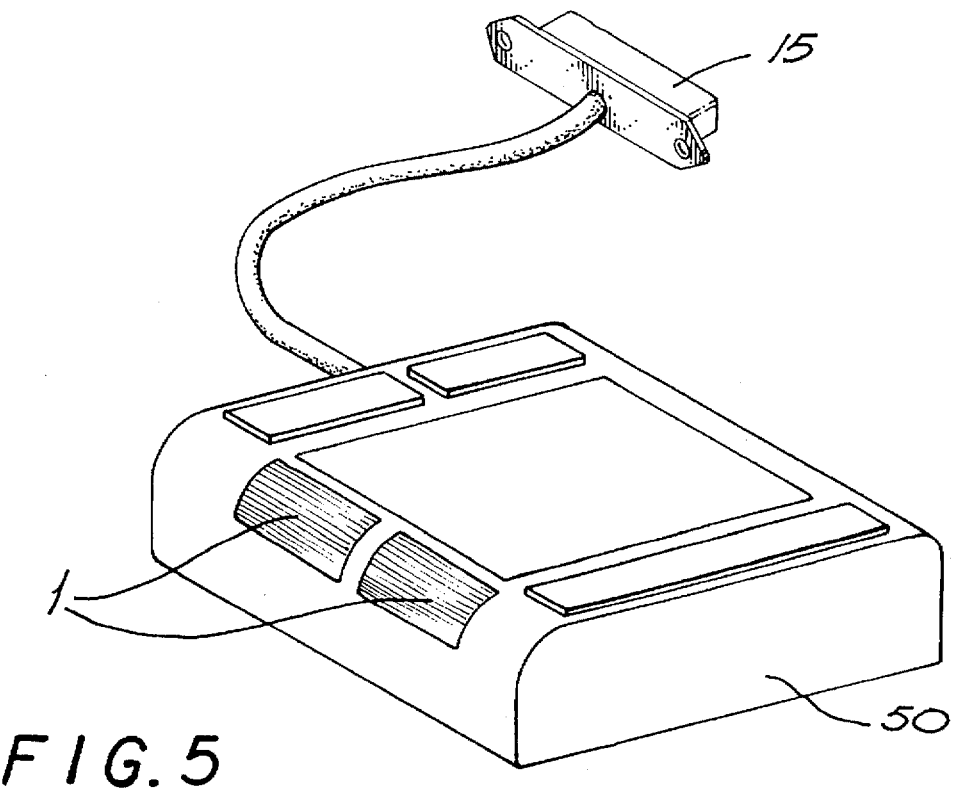
FIG. 5 illustrates a GSR-sensing track pad in accordance with the invention.
Figure 6:
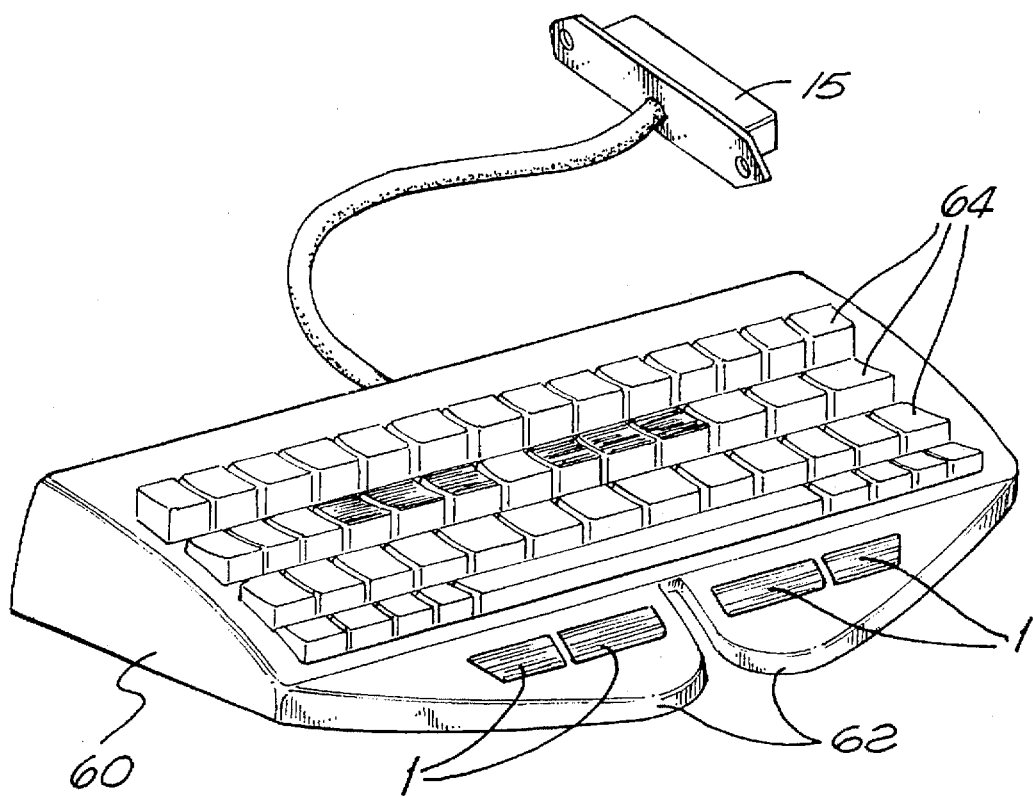
FIG. 6 illustrates a GSR-sensing keyboard in accordance with the invention.

Although the presently preferred embodiment of the invention is in a computer mouse, the invention is not limited in this regard. The invention may also be embodied in other manually operated computer input devices, such as a track ball 40 illustrated in FIG. 4, a track pad 50 illustrated in FIG. 5 or a keyboard 60 illustrated in FIG. 6. Electrodes on keyboard 60 may be located on rests 62 where they will be in contact with the heels of the subject's hands, or they may be located on two or more of the keys 64. If located on the keys, the electrodes are preferably located on the "home" keys so that they will be more frequently in contact with the subject's skin.

Figure 7:
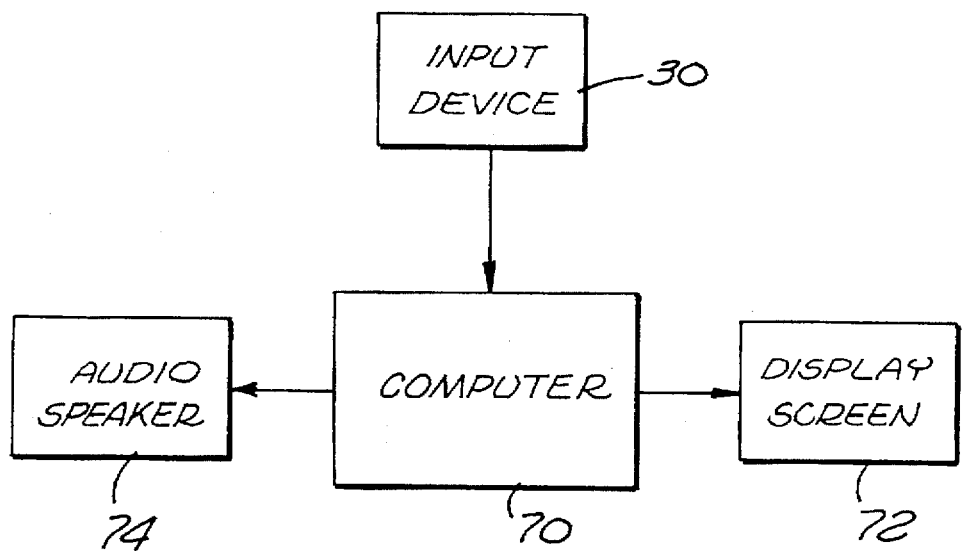
FIG. 7 is a block diagram of a biofeedback system in accordance with the invention.

Referring now to FIG. 7, the computer mouse 30 or other input device with GSR-sensing electrodes 1 is coupled to a serial input port of computer 70. A visual display screen 72 and an audio speaker 74 are also coupled to computer 70. As previously explained, the sensed GSR of the computer user is measured within mouse 30 and a digital value corresponding thereto is sent via the serial connection to computer 70. Software running on computer 70 receives the GSR data and provides audio visual feedback to the computer user. Various feedback responses may be implemented. For example, the computer may advise the user if the GSR reading indicates the presence of stress. Relaxing sounds and/or visual displays may be presented to the user. Alternatively, the user may be coached to perform a quick relaxing breathing exercise to lower the level of stress.

The biofeedback software running on computer 70 may operate concurrently with other application software, or it may run during a dedicated relaxation session. During such a session, the measured GSR may be used to provide a dynamic animated visual and audio feedback to the user. The user-seen image may be animated both in color and in motion in response to the GSR reading. In addition, the characteristics of the music or other audio feedback being played may be modified in tempo, intensity, melody, etc.

The present invention, as a means for measuring the computer user's GSR, is fully compatible with prior art methods and apparatus that utilize such a physiological measurement to provide visual and/or audio feedback to the user. Moreover, since the computer user's physiological state is being continually monitored by computer 70, records of the user's physiological state may be maintained and analyzed. Such analysis can provide valuable information for purposes of improving worker comfort, morale and productivity.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A manually operated computer input device for simultaneously sensing a physiological characteristic of a user and for providing input of data unrelated to the physiological characteristic, said device comprising:

a housing having a surface in at least intermittent contact with the user's skin;

at least one electrode disposed on said surface;

means coupled to said electrode for sensing the physiological characteristic of the user; and manually operated means for inputting data to the computer, said data unrelated to the physiological characteristic.

2. The apparatus of claim 1 wherein the manually operated computer input device is a mouse.

3. The apparatus of claim 1 wherein the manually operated computer input device is a track ball.

4. The apparatus of claim 1 wherein the manually operated computer input device is a track pad.

5. The apparatus of claim 1 wherein the manually operated computer input device is a keyboard.

6. The apparatus of claim 1 wherein the means for sensing a physiological characteristic senses galvanic skin resistance.

7. A biofeedback system comprising:

a computer;

a feedback device coupled to the computer;

a manually operated computer input device having an electrode disposed thereon for contacting the skin of the computer operator;

means coupled to said electrode for sensing a physiological characteristic of the computer operator;

means responsive to said sensed physiological characteristic for providing feedback to the computer operator on the feedback device;

wherein said manually operated computer input device includes means for inputting data to the computer, said data unrelated to the physiological characteristic.

8. The system of claim 7 wherein the manually operated computer input device is a mouse.

9. The system of claim 7 wherein the manually operated computer input device is a track ball.

10. The system of claim 7 wherein the manually operated computer input device is a track pad.

11. The system of claim 7 wherein the manually operated computer input device is a keyboard.

12. The system of claim 7 wherein the feedback presented in response to the sensed physiological characteristic is visual feedback.

13. The system of claim 7 wherein the feedback presented in response to the sensed physiological characteristic is audio feedback.

* * * * *